(12) United States Patent
Zhao

(10) Patent No.: US 12,295,828 B2
(45) Date of Patent: May 13, 2025

(54) VASCULAR RECONSTRUCTION DEVICE

(71) Applicant: SHANGHAI CHUANGXIN MEDICAL TECHNOLOGY CO., LTD, Shanghai (CN)

(72) Inventor: Yimin Zhao, Shanghai (CN)

(73) Assignee: HANGZHOU INNOCARDIAC MEDTECH CO., LTD., Hangzhou (CN)

( * ) Notice: Subject to any disclaimer, the term of this patent is extended or adjusted under 35 U.S.C. 154(b) by 679 days.

(21) Appl. No.: 17/614,378

(22) PCT Filed: May 12, 2020

(86) PCT No.: PCT/CN2020/089717
§ 371 (c)(1),
(2) Date: Nov. 26, 2021

(87) PCT Pub. No.: WO2020/238604
PCT Pub. Date: Dec. 3, 2020

(65) Prior Publication Data
US 2022/0218460 A1      Jul. 14, 2022

(30) Foreign Application Priority Data

May 28, 2019    (CN) .......................... 201910455218.9
Dec. 30, 2019   (CN) .......................... 201911403623.2

(51) Int. Cl.
*A61F 2/07*     (2013.01)
*A61F 2/958*    (2013.01)
*A61F 2/06*     (2013.01)

(52) U.S. Cl.
CPC ................ *A61F 2/07* (2013.01); *A61F 2/958* (2013.01); *A61F 2002/061* (2013.01);
(Continued)

(58) Field of Classification Search
CPC ...... A61F 2/07; A61F 2/958; A61F 2002/061; A61F 2002/075; A61F 2220/0075; A61F 2230/0006; A61F 2230/0067
See application file for complete search history.

(56) References Cited

U.S. PATENT DOCUMENTS 9,808,364 B2 * 11/2017 Roeder ..................... A61F 2/82
2005/0131518 A1 * 6/2005 Hartley .................. A61F 2/856
623/1.13

(Continued)

FOREIGN PATENT DOCUMENTS

| CN | 102458303 A | 5/2012 |
| CN | 205459227 U | 8/2016 |
| CN | 106470646 A | 3/2017 |

OTHER PUBLICATIONS

PCT International Search Report, International Application No. PCT/CN2020/089717.

(Continued)

*Primary Examiner* — Bruce E Snow
(74) *Attorney, Agent, or Firm* — Law Offices of Albert Wai-Kit Chan, PLLC

(57) ABSTRACT

The invention related to medical devices, and in particular to arterial reconstruction devices. The aortic reconstruction device of the present invention is able to conveniently, smoothly, and effectively treat aortic aneurysm or dissection and reconstruct adjacent branch arteries without affecting the vascular perfusion thereof throughout the procedure. The present reconstruction device comprises: a stent graft, and an expansion component, said expansion component may be placed in the stent graft and expands to a size no smaller than the inner diameter of said stent graft.

16 Claims, 18 Drawing Sheets

(52) U.S. Cl.
CPC . *A61F 2002/075* (2013.01); *A61F 2220/0075* (2013.01); *A61F 2230/0006* (2013.01); *A61F 2230/0067* (2013.01)

(56) References Cited

U.S. PATENT DOCUMENTS

2010/0106175 A1    4/2010    McLachlan et al.
2022/0218460 A1*   7/2022    Zhao ........................ A61F 2/958

OTHER PUBLICATIONS

PCT Written Opinion, International Application No. PCT/CN2020/089717.

* cited by examiner graft fenestration opening

VASCULAR RECONSTRUCTION DEVICE

FIELD OF THE INVENTION

The present invention relates to medical equipment, particularly arterial reconstruction devices.

BACKGROUND OF THE INVENTION

Aortic aneurysm and aortic dissection are very dangerous human vascular diseases. Aortic aneurysms originate from diffuse abnormal expansion of blood vessels, with tumor-like rupture as the main risk. Whereas aortic dissection is the result of tearing of the tunica intima of the blood vessel and expansion of the rupture, forming a true and false vascular lumen, which in addition to the risk of rupture, will also severely affect the blood supply of branch vessels or organs.

Aortic aneurysms mainly occur in the abdominal aorta and the thoracic aorta, and the aortic arch may also be involved. At present, endovascular interventional therapy using stent grafts, being minimally invasive, has gradually replaced open surgical procedures, and became the first choice for the treatment of thoracic aortic aneurysms and abdominal aortic aneurysms. However, the following problems still exists: when an aortic aneurysm affects a bifurcated vessel or its nearby areas, in order not to seal or interfere with the normal blood flow of the branch artery, the segment of normal aorta to be used as anchoring area of the stent graft is often limited; and the current consensus on endovascular treatment is that it is necessary to ensure a healthy aorta not less than 15 mm from the neck of the true aneurysm, in order to secure the anchoring of the stent graft. In the case that no sufficient length of healthy aortic segment can be provided for the stent graft, patients often have to choose highly invasive surgery for intervention. At present, stent grafts can be design with a bare area that is sparse at the proximal or distal end to match the bifurcated vessel and increase the anchoring area to a certain extent; the problem is that in order to prevent the bare area of the stent from occluding the branch vessels, the bare area of the stent is often configured very sparsely such that, although it can cover the branch vessels and increase the anchoring area, the bare area of the stent cannot provide sufficient radial supporting force to ensure anchoring, and there is a risk of the stent graft being displaced. For the same reason, there is still no effective and convenient interventional device for endovascular treatment for aortic aneurysms in the aortic arch that are adjacent to the innominate artery, left common carotid artery and left subclavian artery. Surgical treatment is still the mainstream choice, and patients have to face greater surgical trauma and surgical risks.

Aortic dissection often occurs in males aged 50-70, and is the most common cause of death related to the human aorta. The mechanism is mainly derived from the degeneration of the tunica intima of the artery, where the blood flow tears through the tunica intima and enters the tunica media of the artery, causing the separation of the tunica media and forming a dissecting aneurysm. Such harm is very severe, as the mortality rate within one year without treatment is as high as 90%, and the cases of aortic dissection has shown an upward trend domestically in recent years, becoming a major cause for concern. Aortic dissections can be classified into Stanford type A and B according to whether the ascending aorta is affected. Type A affects the ascending aorta, and the proximal rupture may occur in the ascending aorta, aortic arch, or proximal descending aorta. The Type B aortic dissection does not affect the ascending aorta, and the proximal rupture is mainly located in the descending aorta. The current status of treatment is that: for Type A dissection, as the branches of the aortic arch are often affected, it is presently mainly conducted through open surgery, wherein replacement with an artificial blood vessel is performed in the ascending aorta and aortic arch (such as elephant trunk procedure, Sun's procedure), to eliminate the proximal rupture and replace the proximal diseased blood vessels; and for potential distal ruptures, because they are often close to bifurcated arteries, they should be excluded or treated in stages. For Type B dissection, the endovascular treatment method using a stent graft to close the proximal rupture has currently become the first choice, but when the proximal or distal rupture affects the bifurcated artery, there is still no good solution.

In summary, it is difficult to ensure the anchoring of the stent graft for aortic aneurysms or aortic dissections adjacent to bifurcated vessels while ensuring normal blood flow into the bifurcated arteries; examples of which are aortic arch diseases and abdominal aorta diseases. At present, there are some treatment methods such as fenestration techniques and branched stents, but their widespread use is limited by disadvantages such as narrow applicability and difficult operation. The fenestration techniques can be divided into two types, preoperative fenestration and intraoperative fenestration, wherein a 'window' that matches the position of the branch artery is opened on the stent graft while ensuring blood flow into the branch vessel. The difficulty of preoperative fenestration lies in how to accurately align the fenestration to the branch vessels during the operation, while the limitation of intraoperative fenestration is that there is a certain period of time during which the branch arteries will be sealed which often causes ischemic injury, especially at the aortic arch which involves the intracranial blood supply. The limitation of branched stents lies in the diversity of the anatomical positions of bifurcated vessels, as a branched stent with a specific position and size is difficult to adapt to different branch vessel anatomy. Presently, there are also attempts to combine fenestration techniques with implantation of branched stents, but most of them have not been able to put into widespread use or it is difficult to solve the problems of alignment and intraoperative branch artery ischemia.

SUMMARY OF THE INVENTION

The present invention provides an aortic reconstruction device, which can conveniently, smoothly and effectively complete the treatment of aortic aneurysm or dissection and reconstruct the adjacent branch arteries without affecting the blood flow into the adjacent bifurcated arteries. The main working mechanism of the device is as follows: For an aortic aneurysm or aortic dissection adjacent to bifurcated arteries, a stent graft with a temporary diversion channel is first implanted so that blood from the aorta can be directed via the temporary diversion channel to the branch arteries while achieving self-anchorage; and when performing intraoperative fenestration on the stent graft at the ostium of the branch artery, blood flow into the branch arteries can still be maintained during the intraoperative fenestration process due to the temporary diversion channel on the stent graft; and after the fenestration is completed or when branch stent grafts are further implanted in the branch arteries, a bare stent or balloon expansion or other expansion mechanisms can be inserted to expand and restore the temporary diversion channel to the tube shape of the main body of the stent graft so as to achieve complete reconstruction of the aorta and adjacent bifurcated vessels, without affecting the blood flow of branch vessels during the whole process.

In one embodiment, the present invention provides an aortic reconstruction device comprising: a stent graft (100) with a temporary diversion channel, and a bare stent (200); as shown in FIG. 1A, the stent graft (100) has a main body comprising a stent frame and a graft covering said stent frame, said main body may comprise a first stent graft section (110) (the end of the stent graft closer to the heart, hereinafter referred to as the proximal end), a second stent graft section (120), and a third stent graft section (130) (the end of the stent graft further away from the heart, hereinafter referred to as the distal end); wherein the second stent graft section is configured with a fenestration area (121). The surface of the stent graft (100) comprises at least one temporary diversion channel (140), said at least one temporary diversion channel may further comprise a proximal channel (141), a fenestration area channel (142), and a distal channel (143). The proximal channel (141) is located in the first stent graft section (110), the fenestration area channel (142) is contained in the fenestration area (121), and the distal channel (143) is located in the third stent graft section (130). The fenestration area (121) corresponds to one or more adjacent branch arterial openings, and the function of the temporary diversion channel (140) is that when the stent graft (100) is implanted into the blood vessel, blood can be directed through the temporary diversion channel (140) to the adjacent bifurcated arteries, and blood flow will not be affected due to blockage of the branch arteries during the fenestration. When the intraoperative fenestration is completed in the fenestration area (121), or after branch stent grafts are further implanted in the branch arteries, the temporary diversion channel (140) can be expanded to alter its concave state, forming a complete tube shape with the stent graft (100).

In one embodiment, the aortic reconstruction device of the present invention is used to repair one or more proximal dissection ruptures in the aortic arch.

DETAILED DESCRIPTION OF THE INVENTION

Figure 1A:
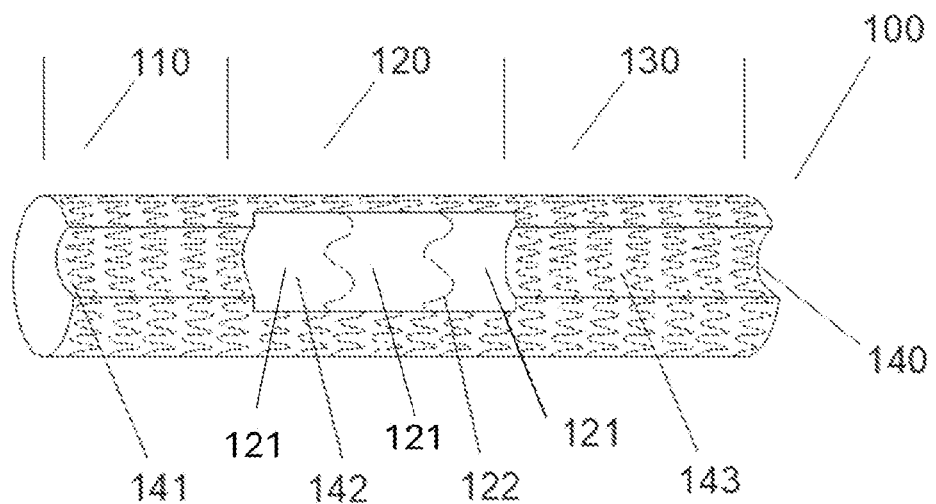
FIG. 1A is a stent graft (100) of the present invention, said stent graft has a main body comprising a stent frame and a graft covering said stent frame, and may comprise a first stent graft section (110) (the end of the stent graft closer to the heart), a second stent graft section (120) and a third stent graft section (130) (the end of the stent graft further away from the heart); wherein the second stent graft section is configured with a fenestration area (121). The surface of the stent graft (100) comprises at least one temporary diversion channel (140), and may further comprise a proximal channel (141), a fenestration area channel (142), and a distal channel (143). The proximal channel (141) is located in the first stent graft section (110), the fenestration area channel (142) is contained in the fenestration area (121), and the distal channel (143) is located in the third stent graft section (130). The fenestration area (121) corresponds to one or more ostium of adjacent branch arterties. Adjacent fenestration areas (121) are separated by a concave skeletal structure (122).

The present invention provides a vascular reconstruction device comprising a stent graft. In one embodiment, said stent graft comprises a main body which comprises a frame and a graft, characterized in that: said main body comprises a fenestration area having only graft; and said stent graft has a surface comprising at least one temporary diversion channel, said temporary diversion channel is connected with said fenestration area.

In one embodiment, said temporary diversion channel is expandable to fix said stent graft into a circular cross-section.

In one embodiment, said temporary diversion channel further comprises more than one fenestration area, each fenestration area is separated by a concave skeletal structure.

In one embodiment, said concave skeletal structure is connected or not connected to the frame of said main body.

In one embodiment, said temporary diversion channel has a cross-section wider than other parts at where said temporary diversion channel is connected with said fenestration area.

In one embodiment, said fenestration area is located at an end of said main body and has concave features.

In one embodiment, said main body comprises a first stent graft section, a second stent graft section, and a third stent graft section, said fenestration area is located in the second stent graft section. In one embodiment, said temporary diversion channel is connected to the fenestration area of the second stent graft section via the first stent graft section or the third stent graft section. In one embodiment, said second stent graft section is more flexible than the first stent graft section or the third stent graft section.

In one embodiment, the shape of said stent graft is selected from the group consisting of a partially bulged outward or inwardly concaved shape, a straight cylindrical shape, a cone shape, or a curved shape.

In one embodiment, said temporary diversion channels are distributed on the stent graft surface linearly along length direction of the stent graft, spiral-linearly or any other curved trajectory along the stent graft surface.

In one embodiment, said temporary diversion channel is connected with at least one end of said stent graft.

In one embodiment, said stent graft comprises a control mechanism to control opening and closing of said at least one temporary diversion channel. In another embodiment, said control mechanism is located in a part of said stent graft having at least one temporary diversion channel, the frame and the graft forming said at least one temporary diversion channel do not connect, at least one suture ring is provided on each of a same side and an opposite side of said at least one temporary diversion channel, and at least one control wire is provided for opening and closing said at least one temporary diversion channel of the graft.

In one embodiment, said stent graft is internally configured with a suture ring and a control wire, and the temporary diversion channel comprises a graft with a controllable shape. In one embodiment, both the stent graft and the temporary channel formed by the graft can be controlled. In another embodiment, said stent graft has a circular cross-section.

The present invention further provides a vascular reconstruction device. In one embodiment, said vascular reconstruction device comprises:
A stent graft according to the present invention; and an expansion component to be placed in said stent graft for expansion to not less than inner diameter of said stent graft.

In one embodiment, said expansion component is a bare stent. In one embodiment, said bare stent comprises an area corresponding to said fenestration area, and said area comprises a sparse mesh.

In one embodiment, the expansion component is a balloon.

The present invention further provides a method of using the vascular reconstruction device of the present invention. In one embodiment, said method comprises the following steps: a) inserting said stent graft through a catheter into a blood vessel in need, said blood vessel comprises at least one branch vessel: b) placing the temporary diversion channel of said fenestration area outside said at least one branch vessel to provide blood to the at least one branch vessel; c) performing graft fenestration at a location corresponding to the branch vessel within said fenestration area: and d) inserting said expansion component into said stent graft through a catheter and expanding said stent graft to form a fixed circular cross-section that pushes against inner wall of said blood vessel.

In one embodiment, said step c) further comprises inserting a branch stent graft at said location corresponding to the branch vessel. In one embodiment, the proximal end of said branch graft comprises a flared mouth, and step (d) comprises pushing said flared mouth tightly against the graft of the fenestration area using the expansion component.

In one embodiment, said expansion component is a bare stent. In one embodiment, the bare stent comprises an area corresponding to said fenestration area, and said area comprises a sparse mesh.

In one embodiment, said expansion component is a balloon.

In one embodiment, said expansion component is withdrawn from the blood vessel after completing step (d).

In one embodiment, said step (b) further comprises opening said temporary diversion channel with a control mechanism. In another embodiment, said control mechanism comprises a control wire, a suture ring, and a frame and graft that are not connected, and said temporary diversion channel will open by pulling said control wire.

Example 1

In one embodiment, the present invention provides an aortic reconstruction device comprising: a stent graft (100) with a temporary diversion channel, and a bare stent (200); as shown in FIG. 1A, the stent graft (100) has a main body comprising a stent frame and a graft covering said stent frame, said main body may comprise a first stent graft section (110) (the end of the stent graft closer to the heart, hereinafter referred to as the proximal end), a second stent graft section (120), and a third stent graft section (130) (the end of the stent graft further away from the heart, hereinafter referred to as the distal end); wherein the second stent graft section is configured with a fenestration area (121). The surface of the stent graft (100) comprises at least one temporary diversion channel (140), and said at least one temporary diversion channel may further comprise a proximal channel (141), a fenestration area channel (142), and a distal channel (143). The proximal channel (141) is located in the first stent graft section (110), the fenestration area channel (142) is contained in the fenestration area (121), and the distal channel (143) is located in the third stent graft section (130). The fenestration area (121) corresponds to one or more adjacent branch arterial openings, and the function of the temporary diversion channel (140) is that when the stent graft (100) is implanted into the blood vessel, blood can be directed through the temporary diversion channel (140) to the adjacent bifurcated arteries, and blood flow will not be affected due to blockage of the branch arteries during the fenestration. When the intraoperative fenestration is completed in the fenestration area (121), or after branch stent grafts are further implanted in the branch arteries, the temporary diversion channel (140) can be expanded to alter its concave state, forming a complete tube shape with the stent graft (100).

Figure 1B:
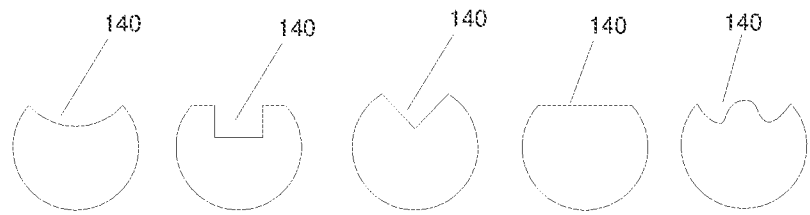
FIG. 1B shows cross-sections of temporary diversion channels (140), which can be arc-shaped, groove-shaped, V-shaped, linear, or any other shapes.
Figure 1C:
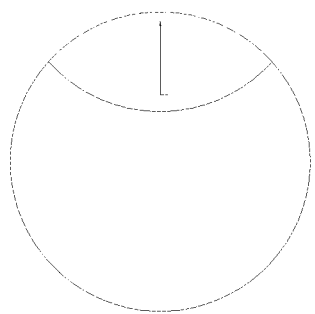
FIG. 1C shows that the temporary diversion channel (140) can be expanded to form a cylindrical shape with the main body of the stent graft, that is, each cross-section expands into a complete circle without changing its circumference.

As shown in FIG. 1B, the temporary diversion channel (140) (comprising a proximal channel (141), a fenestration area channel (142), and a distal channel (143)) may have a cross-section that is arc-shaped, groove-shaped, V-shaped, linear, or any other shapes as long as part of it does not form a complete cylinder; the temporary diversion channel (140) is expandable to form a cylindrical shape with the main body of the stent graft. Preferably, it is a circular arc concave shape, formed by a partial circular arc concave shape of the circular cross section, that is, each cross-section expands into a complete circle without changing its circumference, as shown in FIG. 1C.

Figure 1D:
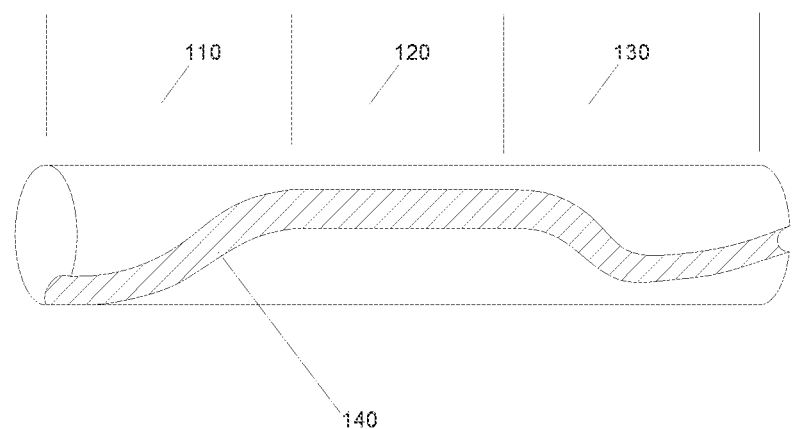
FIG. 1D shows the temporary diversion channel (140) being distributed along the surface of the stent graft in a spiral-linear or any other curved trajectory.

In one embodiment, the temporary diversion channel (140) can be distributed (linearly) along the length of the stent graft, or can be distributed along the surface of the stent graft in a spiral-linear or any other curved trajectory, in order to avoid the possible tunica intima dissection of the blood vessel, thus avoiding blockage of the temporary diversion channel; as shown in FIG. 1D.

Example 2

Figure 2A:
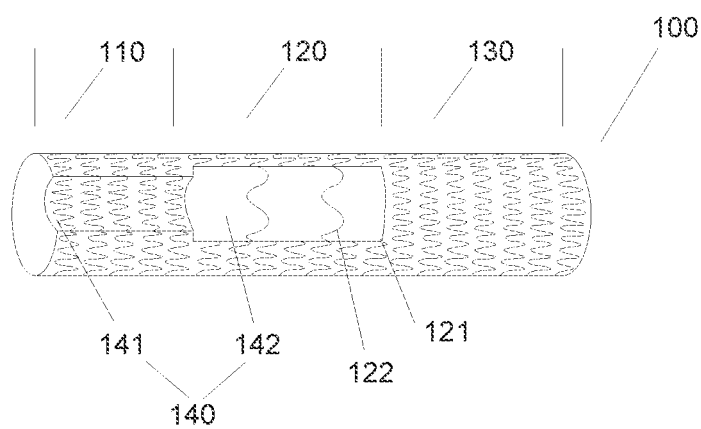
FIG. 2A shows the temporary diversion channel (140) being initiated from the first stent graft section (110), that is, proximally, and ends after extending through the second stent graft section (120).
Figure 2B:
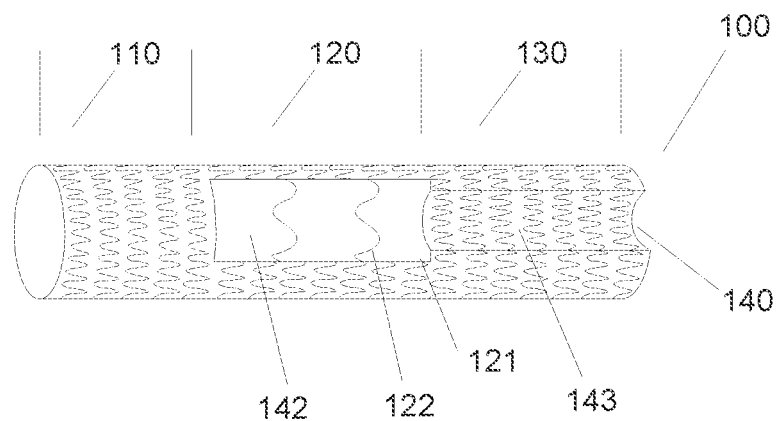
FIG. 2B shows the temporary diversion channel (140) being initiated from the third stent graft section (130), that is, distally, and ends after extending to the second stent graft section (120).

In one embodiment, optionally, the temporary diversion channel (140) may not penetrate along entire length of the stent graft, that is, the temporary diversion channel (140) may be initiated from the first stent graft section (110) (which is the proximal end), extending through and ending after the second stent graft section (120), as shown in FIG. 2A, or it can continue to extend to the third stent graft section (130) without penetrating through it; or the temporary diversion channel (140) can be initiated at the third stent graft section (130) (which is the distal end), extending through and ending after the second stent graft section (120), as shown in FIG. 2B, or it can continue to extend to the first stent graft section (110) without penetrating through it.

In one embodiment, the three parts of the temporary diversion channel (140), that is, the proximal channel (141), the fenestration area channel (142), and the distal channel (143) can be configured with the same or different cross-sectional shapes, and the same or different channel cross-sectional area; preferably, the fenestration area channel (142) has a larger cross-sectional width than the proximal channel (141) and the distal channel (143). Similarly, each channel (proximal channel (141), fenestration area channel (142), distal channel (143)) itself can be configured with a uniform or gradual changing cross section.

In one embodiment, the second stent graft section (120) comprises one or more fenestration areas (121).

In one embodiment, the fenestration areas (121) have an area with no metal frame and only comprises a graft material, and adjacent fenestration areas (121) are separated by a concave skeletal structure (122).

In one embodiment, when the second stent graft section comprises only one fenestration area, there may be no concave skeletal structure. The function of the concave skeletal structure (122) is to allow the graft at the fenestration area (121) to form and to maintain the shape of the concave channel. The shape of the concave skeletal structure (122) may be a concave circular arc structure, a concave wave-like structure, or a plurality of concave V-shaped structures. The concave skeletal structure (122) can be connected or not connected with the stent body of the second stent graft section (120).

In one embodiment, the concave skeletal structure (122) may be metallic materials such as stainless steel wire, nickel-titanium alloy wire, etc., or other shapable non-metallic materials, such as nylon, polytetrafluoroethylene, etc.; preferably, it is a non-metallic material that can be destroyed by laser or other fenestration methods.

Example 3

Figure 3A:
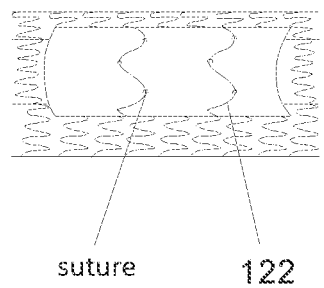
FIG. 3A shows the concave skeletal structures (122) being connected by one or more suture points using sutures at the graft in the fenestration area (121).
Figure 3B:
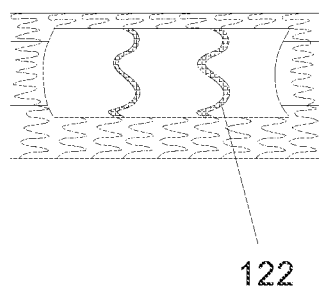
FIG. 3B shows the concave skeletal structures (122) being configured in a belt-like structure in the fenestration area (121), which is woven together with the graft.
Figure 3C:
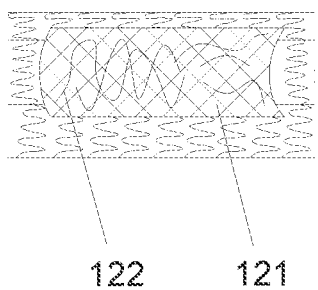
FIG. 3C shows the concave skeletal structures (122) being implemented using a shapable non-metallic wire, which is continuously or discontinuously woven with the graft wires in the fenestration area 122 into a single body, that is, the entire fenestration area (121) with concave skeletal structures (122) possesses the plasticity for forming the concaved shape yet can be expanded unlike the other areas of the stent graft.

In one embodiment, the concave skeletal structure (122) can be connected with the graft of the fenestration area (121) through one or more suture points via sutures, as shown in FIG. 3A. Optionally, the concave skeletal structure (122) can also be in the form of a belt-like structure in the fenestration area (121) that is woven together with the graft, as shown in FIG. 3B. Optionally, the concave skeletal structure (122) can also be implemented using a shapable non-metallic wire, which is continuously or discontinuously woven with the graft wires in the fenestration area (121) into a single body, that is, the entire fenestration area (121) with concave skeletal structures (122) possess the plasticity for forming a fixed concave shape yet can be expanded unlike the graft characteristics of other areas, as shown in FIG. 3C. The fenestration area is configured without a metal frame, only having a graft, and is configured with sparse concave skeletal structures (122) or non-metallic concave skeletal structures (122) to avoid as much as possible any interference by the metal frame during intraoperative fenestration, thereby improving the success rate of fenestration and subsequent implantation of branch stent grafts. Preferably, the circumferential width of the fenestration area (121) is greater than the diameter of the branch artery, so as to ensure that the fenestration area and the branch artery have sufficient space for alignment, such that the branch artery is always aligned with the graft at the fenestration area; for example, for its application in the aortic arch, the circumferential width of the fenestration area (121) may range from 0.5 cm to 5 cm.

The first stent graft section (110) and the third stent graft section (130) will mainly assume the role of anchoring the stent graft during surgery. Due to the anatomical needs of specific diseases (such as distorted aneurysms, aortic arch lesions, etc.), the stent is required to have a certain degree of flexibility. As mentioned above, each section of the stent graft can be configured with the same or different radial supporting forces. Preferably, the supporting forces of the first stent graft section (110) and the third stent graft section (130) are greater than that of the second stent graft section (120), and the second stent graft section (120) is more flexible than the other two sections. The implementation method is as follows: when the main body is a wavy metal wire unit, it can be implemented by changing the wire diameter, using different design dimensions of the wavy structural unit, and using different densities of the wavy structural unit; for example, when the main body of the stent is a cutting tube stent, it can be implemented by configuring different lengths, widths and angles of the tube; and for example, when the main body of the stent is a braided stent, the above-mentioned different supporting forces can be achieved through different braiding densities. Alternatively, the three stent graft sections can each be implemented with different processing techniques, such as using wavy frame structures, weaving, cutting, 3D printing, etc., in order to achieve different performance effects for each segment.

Example 4

Figure 4A:
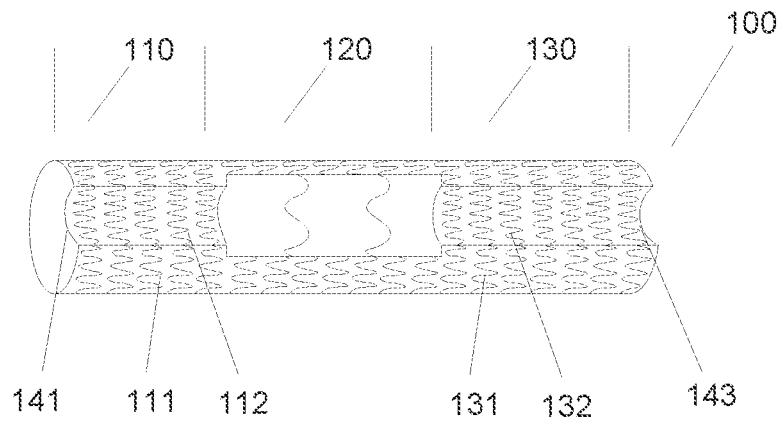
FIG. 4A shows a stent graft (100), the frame structure of the first stent graft section (110) comprises a proximal stent main body (111) and a proximal stent channel (112); the frame structure of the third stent graft section (130) comprises a distal stent main body (131) and a distal stent channel (132).

For the stent graft (100) as described above, the first stent graft section (110) has a frame structure comprising a proximal main body stent (111) and a proximal channel stent (112); the third stent graft section (130) has a frame structure comprising a distal main body stent (131) and a distal channel stent (132), as shown in FIG. 4A. The proximal main body stent (111) and the proximal channel stent (112) can be configured with the same or different stiffness. Similarly, the distal main body stent (131) and the distal channel stent (132) can be configured with the same or different stiffness. In order to enable the proximal channel stent (112) and the distal channel stent (132) to be easily expanded by subsequently implanted bare stents, balloons or other expansion mechanisms, preferably, the proximal channel stent (112) has a lower stiffness compared with the main body stent (111) of the same section, and the distal channel stent (132) has a lower stiffness compared with the main body stent (131) of the same section. Wherein, the proximal channel stent (112) can be connected or not connected to the proximal main body stent (111), the two stents can also select the same or different structural units, and the same or different materials and manufacturing processes; and wherein, the distal channel stent (132) can be connected or not connected to the main body stent (131), the two stents can also select the same or different structural units, and the same or different materials and manufacturing processes.

For the stent graft (100) as described above, the frame of the main body can be made of stainless steel, nickel-titanium alloy, or cobalt-chromium alloy, and can be a wire or a tube.

For the stent graft (100) as described above, the main body can be a cylindrical shape with a constant diameter, a tapered shape with a gradually changing diameter, or a curved shape suitable for the anatomical structure of the application.

Figure 4B:
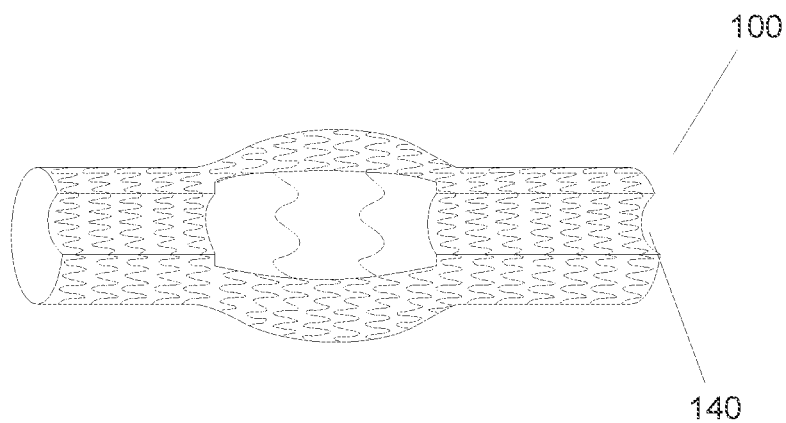
FIG. 4B shows the stent graft (100) partially bulging outward to reduce the distance between the branch arterial ostium on the aneurysm and the fenestration area (121).

In one embodiment, the stent graft (100) as described above can partially bulge outward, which is beneficial to the application when the aneurysm contains bifurcated arteries, that is, the distance between the branch arterial opening on the aneurysm and fenestration area (121) is decreased, in order to facilitate the fenestration and the potential subsequent implantation of the branch stent grafts, as shown in FIG. 4B. Also optionally, it can be partially concaved.

For the stent graft (100) as described above, preferably, its proximal and distal diameters are not less than the diameter of the blood vessel at the corresponding implantation site.

For the stent graft (100) as described above, its graft can be located at the outer or inner surfaces of the stent frame structure, or both the inner and outer surfaces are configured with a graft. Optionally, the material of the graft may be polyethylene terephthalate (PET), polytetrafluoroethylene (PTFE), silica gel, etc.

When the stent graft (100) is not configured with a temporary diversion channel at its distal end, optionally, its distal graft can extend beyond the main body to form a stent-free skirt, in order to facilitate possible additional surgical operations in the future.

Example 5

Figure 5A:
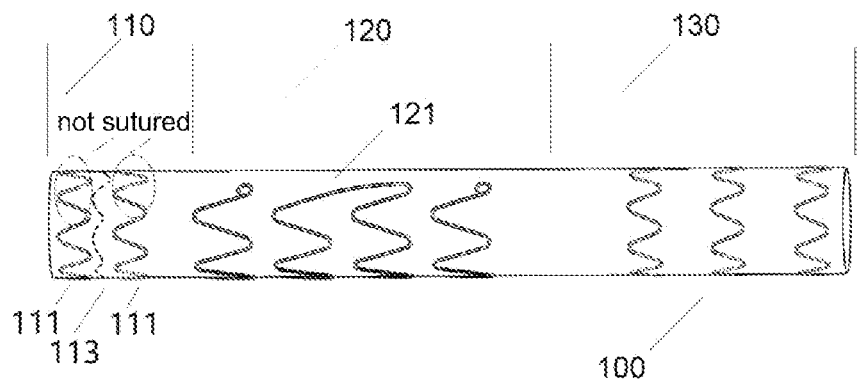
FIG. 5A shows a stent graft (100), the first stent graft section (110) comprises a main stent body (111) disposed outside the graft and partly joined with the graft, and an internal stent body (113) disposed inside the graft and completely joined with the graft; the second stent graft section (120) comprises a fenestration area (121), and the fenestration area (121) does not contain a skeletal structure.
Figure 5B:
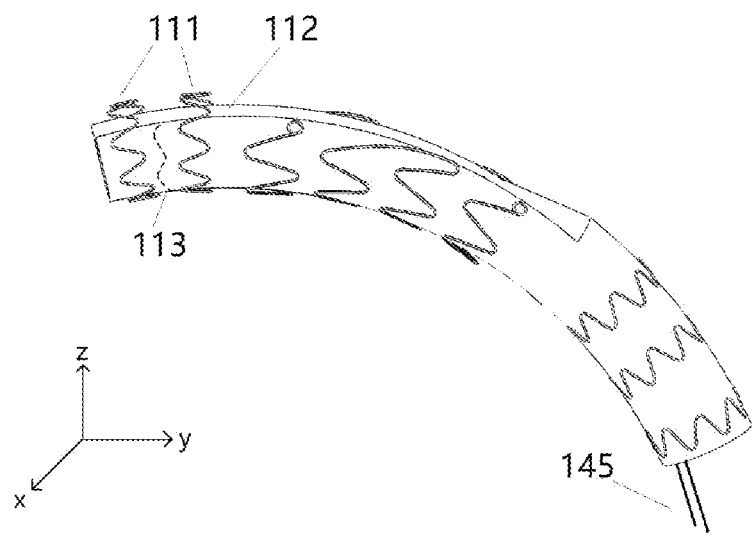
FIG. 5B shows the above-mentioned stent graft (100), the temporary diversion channel (140) is in an open state and controlled to bend into a preset configuration.

In one embodiment, the cross-section of the stent graft (100) is circular, and the temporary diversion channel (140) comprises a graft with a controllable shape. As shown in FIG. 5A and FIG. 5B, the first stent graft section (110) comprises a main body stent (111) disposed outside the graft and partially joined with the graft, and an internal stent (113) disposed inside the graft and completely joined with the graft; the second stent graft section (120) comprises a fenestration area (121), and the fenestration area (121) does not comprise a skeletal structure, such that the graft of the first stent graft section (110) and the second stent graft section (120) can be moved, and it can become a temporary diversion channel (140) when it is recessed.

Figure 5C:
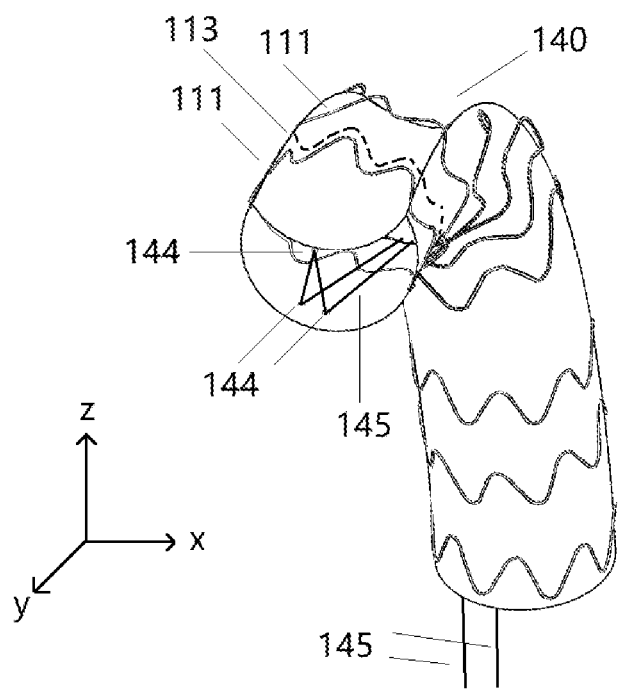
FIG. 5C shows the above-mentioned stent graft (100), wherein at least one suture ring (144) is provided on each of the same side and the opposite side of the temporary diversion channel (140) at the proximal end of the graft, and at least one control wire (145) is provided for opening and closing the temporary diversion channel (140) of the graft. First, from the handle, the control wire (145) passes from the distal end towards the proximal end through the suture ring (144) at the opposite side of one or more temporary diversion channels (140), then the control wire (145) passes from the proximal end towards the distal end through the suture ring (144) at the same side of one or more temporary diversion channels (140), and finally the control wire (145) passes from the proximal end towards the distal end through the suture ring (144) at the opposite side of one or more temporary diversion channels (140).

In one embodiment, as shown in FIG. 5C, at least one suture ring (144) is disposed on the same side and the opposite side of the temporary diversion channel (140) at the proximal end of the graft, and at least one control wire (145) is provided for opening and closing the temporary diversion channel (140) of the graft. First, from the handle, the control wire (145) passes from the distal end towards the proximal end through the suture ring (144) at the opposite side of one or more temporary diversion channels (140), then the control wire (145) passes from the proximal end towards the distal end through the suture ring (144) at the same side of one or more temporary diversion channels (140), and finally the control wire (145) passes from the proximal end towards the distal end through the suture ring (144) at the opposite side of one or more temporary diversion channels (140). In FIGS. 5B and 5C, the suture rings (144) are respectively configured on the midline and the opposite side of the temporary diversion channel (140). When the control wire (145) is pulled, the temporary diversion channel (140) is opened, and the stent graft (100) is bent around the x-axis. It should be understood that if multiple control wires (145) and corresponding suture rings (144) are configured in the circumferential direction of the stent graft (100), the control of the shape of the temporary diversion channel (140) can be strengthened, and the stent graft (100) can be rotated around the x, y, and z axes as shown by the coordinates in the figure, strengthening its ability to adhere to the blood vessel at bent areas, thereby improving the "bird's beak" and endoleak problems.

In one embodiment, the above-mentioned stent graft (100) is placed on the target blood vessel, and the fenestration area (121) corresponds to the branch vessel. At this time, if the operator simultaneously pulls both ends of the control wire (145) at the distal end of the handle, the temporary diversion channel (140) is fully opened, and at the same time, as the amount of traction increases, the stent graft (100) will bend into a preset configuration until it fits tightly with the blood vessel wall; on the contrary, if the control wire (145) is released, due to the resilience of the internal stent (113) at the proximal end, the temporary diversion channel (140) will automatically close. After completing the fenestration and implanting the branch stent, the operator continuously pulls one end of the control wire (145) from the distal end of the handle, and the control wire (145) can be completely withdrawn from the subject's body through the handle.

After the above-mentioned stent graft (100) has been implanted in the aorta, the fenestration is performed at the fenestration area corresponding to the branch artery, or after the branch stent graft is further implanted in the branch artery through the fenestration, a bare stent can be further implanted to expand the temporary diversion channel and restore it to the tubular shape of the stent graft main body.

Figure 6:
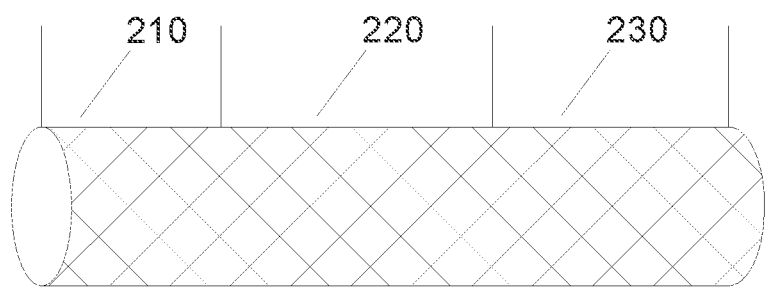
FIG. 6 shows a bare stent (200), which comprises a first bare stent section (210), a second bare stent section 220, and a third bare stent section (230) respectively corresponding to the first stent graft section (110), the second stent graft section (120), and the third stent graft section (130).

The bare stent (200) as mentioned above comprises a first bare stent section (210), a second bare stent section (220), and a third bare stent section (230), they correspond to the first stent graft section (110), the second stent graft section (120), and the third stent graft section (130), as shown in FIG. 6.

The bare stent (200) as mentioned above has a diameter larger than the inner diameter of the stent graft (100) to ensure that the temporary diversion channel (140) on the stent graft (100) is expanded and that it is firmly anchored relative to the stent graft (100); at the same time, it can ensure that the branch stent graft in the fenestration area (121) is closely attached to the graft, in order to reduce the risk of endoleaks.

In one embodiment, for the bare stent (200) as described above, the main body may be a stent shaped by cutting and expanding, or a braided stent, or may be realized by a mixture of both cutting and braiding processes. The material of the bare stent can be stainless steel, nickel-titanium memory alloy, cobalt-chromium alloy, etc., and can be a wire or a tube.

In one embodiment, optionally, for the bare stent (200) as described above, the radial supporting force of its first bare stent section (210) and third bare stent section (230) are greater than that of the second bare stent section (220); optionally, the second bare stent section (220) has better flexibility than the first bare stent section (210) and the third bare stent section (230). The above-mentioned characteristics can be realized by configuring different parameters such as mesh density, tube diameter, and wire diameter.

In one embodiment, optionally, the bare stent (200) as described above has a sparser mesh in the area corresponding to the fenestration area (121) of the stent graft (100) as compared to other areas, to ensure that the blood flow into the branch arteries after subsequent fenestrations will not be affected by the bare stent.

In one embodiment, as compatible with the above-mentioned stent graft (100), the main body of the bare stent (200) can be a cylindrical shape with a constant diameter, or a tapered shape with a gradually changing diameter, or a partially convex or concave contoured configuration.

Figure 7:
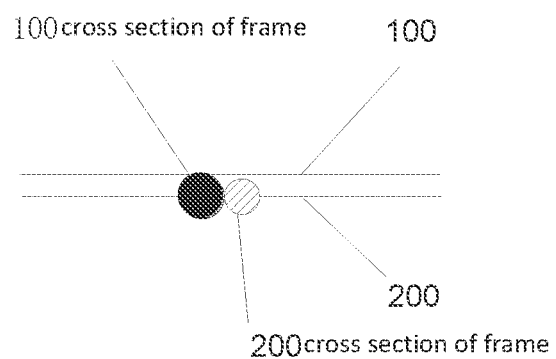
FIG. 7 shows the stent frame part of the stent graft (100) being trapped into the bare stent (200) as a result of the grid feature at the bare stent (200).

In one embodiment, optionally, while the bare stent (200) is able to expand the above-mentioned stent graft (100), it is also further configured with one or more anchoring mechanisms relative to the stent graft, which can be realized by mutual snapping between the frame structure of two stents, an example of the cross section of such mutual snapping is shown in FIG. 7. This can be achieved by configuring a grid feature for the bare stent (200) such that the stent frame part of the stent graft (100) is trapped therein. For example, when the frame structure of the stent graft (100) is a wave-shaped unit, the bare stent (200) can be partially configured with similar wave-shaped units, and the two can be matched to form an interlocking anchor mechanism.

Depending on the anatomical and treatment strategy needs, optionally, the length of the bare stent (200) can be greater than, equal to, or less than the length of the above-mentioned stent graft (100).

Optionally, outside those area corresponding to the fenestration area (121) of the stent graft, the bare stent can be partially configured with a graft, such as configuring a graft in the first bare stent section (210) and the third bare stent section (310).

Optionally, the distal end of the bare stent (200) can be configured with a graft and extend beyond the frame of the bare stent, to facilitate possible additional surgical operations in the future.

Optionally, the material of the above-mentioned graft may be polyethylene terephthalate (PET), polytetrafluoroethylene (PTFE), silica gel, etc.

Example 6

Figure 8A:
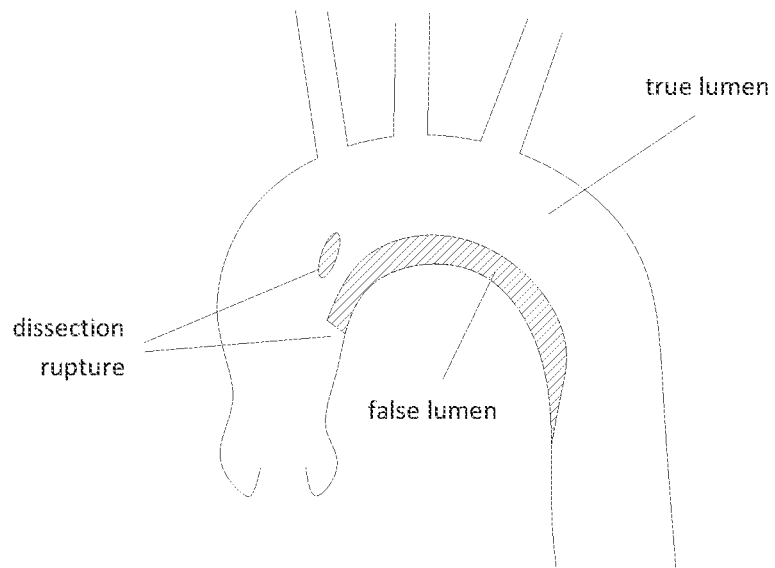
FIG. 8A shows that there are one or more proximal dissection ruptures at the aortic arch, and a true lumen and false lumen have started forming through the proximal ruptures.

For the above-mentioned stent graft (100), taking the aortic dissection of the arch as an example, the implantation process is as follows:

In one embodiment, as shown in FIG. 8A, there are one or more proximal dissection ruptures in the aortic arch, and a true lumen and false lumen have started forming through the proximal ruptures.

Figure 8B:
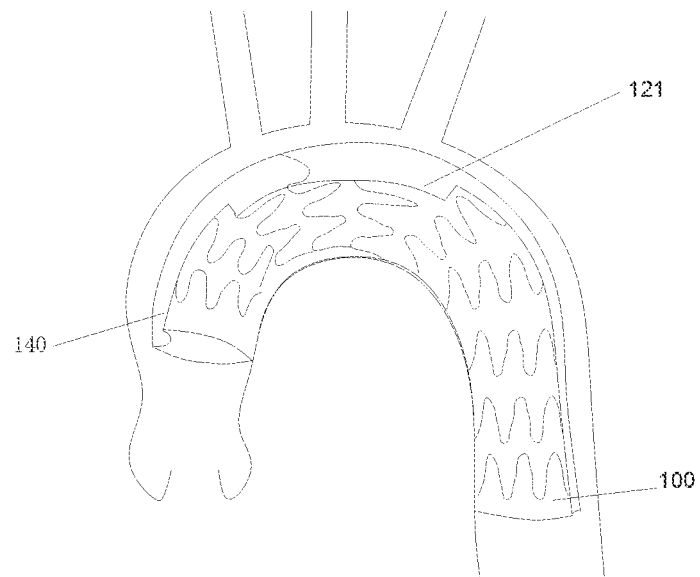
FIG. 8B shows a stent graft (100) with a temporary diversion channel being implanted via a transcatheter procedure, and the dissection rupture is blocked by the stent graft (100), but each branch vessel of the aortic arch can still pass through the temporary diversion channel (140) to achieve normal blood flow.

As shown in FIG. 8B, the stent graft (100) with a temporary diversion channel is implanted via a transcatheter procedure, and the dissection rupture is blocked by the stent graft (100), but each branch vessel of the aortic arch can still pass through the temporary diversion channel (140) to achieve normal blood flow.

Figure 8C:
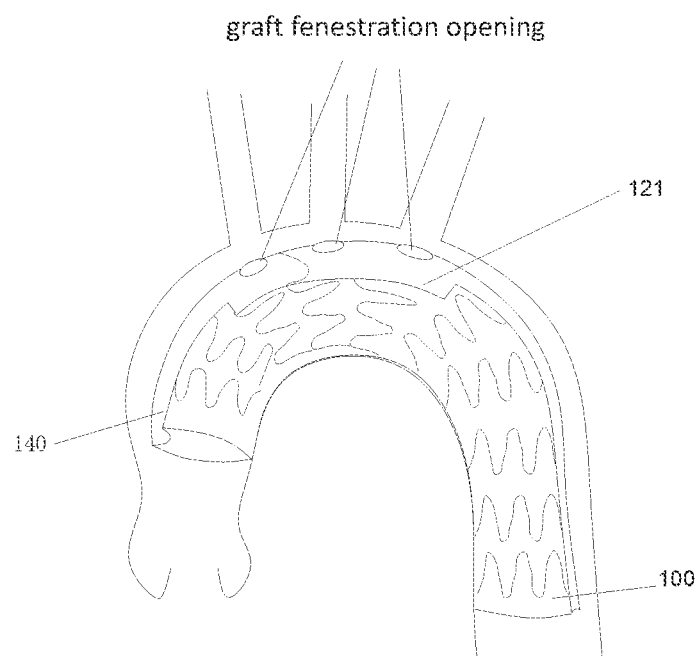
FIG. 8C shows the fenestration area undergoing graft fenestration via the blood vessel path, the fenestration area (121) of the stent graft (100) has no metal frame, or the concave frame is made of non-metallic materials.
Figure 8D:
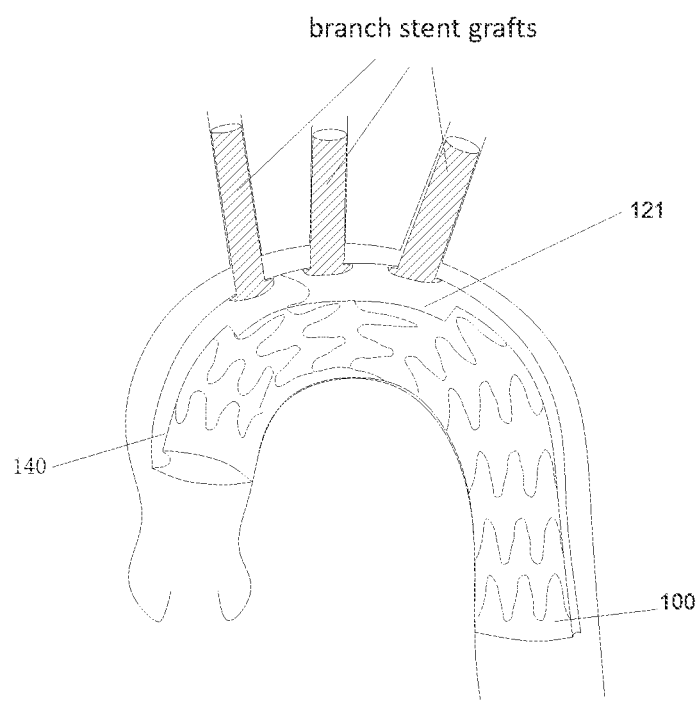
FIG. 8D shows branch stent grafts (100) being implanted, and the fenestration area (121) of the stent graft (100) has no metal frame.

As shown in FIG. 8C, the fenestration area further undergoes graft fenestration via the blood vessel path, the fenestration area (121) of the stent graft (100) has no metal frame, or the concave frame is made of non-metallic materials, thereby avoiding any interference by the metal frame during the fenestration. Branch stent grafts (100) may be further implanted as shown in FIG. 8D, and the fenestration area (121) of the stent graft (100) with no metal frame also ensures the smooth implantation and expansion of the branch stent graft.

Figure 8E:
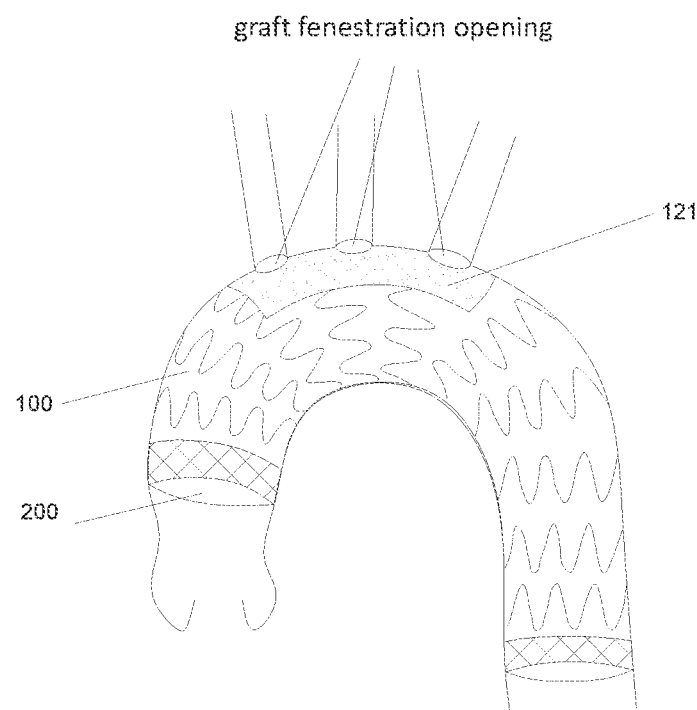
FIG. 8E shows that after the bare stent (200) is implanted via a transcatheter procedure, the stent frame of the proximal channel (141) and distal channel (143) are expanded, the fenestration area channel (142) is also expanded, and the graft is attached to the blood vessel wall by the bare stent (200).
Figure 8F:
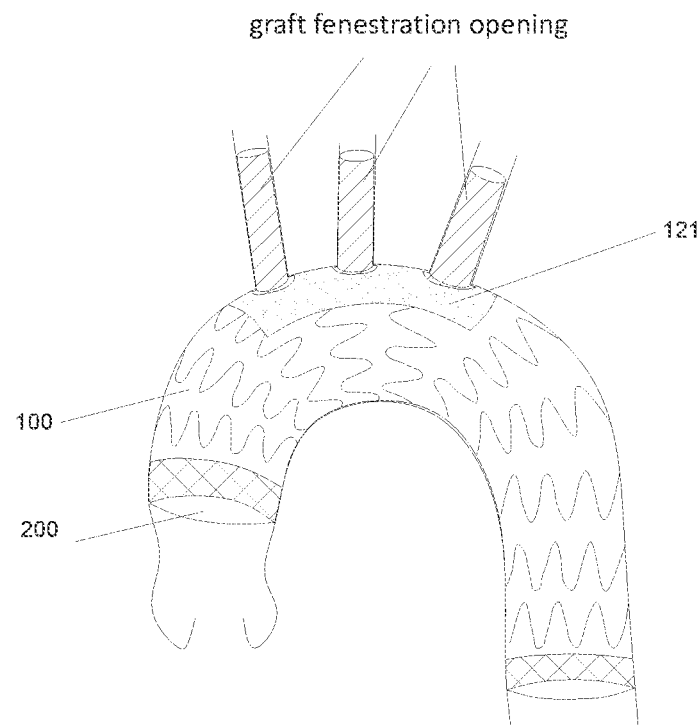
FIG. 8F shows the branch stent grafts being implanted, the bare stent (200) expands the proximal channel (141) and the distal channel (143).
Figure 8G:
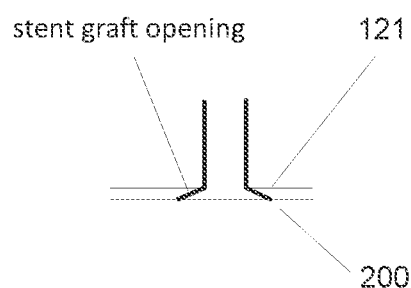
FIG. 8G shows that when the branch stent grafts being implanted as shown in FIG. 8F, the bare stent (200) pushes the flared mouth of the proximal end of the branch stent graft against the fenestration area (121).

As shown in FIG. 8E, the bare stent (200) is implanted via a transcatheter procedure, the stent frame of the proximal channel (141) and distal channel (143) are expanded; the fenestration area channel (142) is also expanded, and the graft is pushed against the blood vessel wall by the bare stent (200). When branch stent grafts (100) are implanted as shown in FIG. 8F, the bare stent (200) expands the proximal channel (141) and the distal channel (143), while at the same time, the bare stent (200) pushes the flared mouth of the proximal end of the branch stent grafts against the graft in the fenestration area (121) to ensure that there is no endoleak, as shown in FIG. 8G.

For the stent graft (100) as described above, if the main stent frame (including the temporary diversion channel stent frame) is made by cutting and shaping stainless steel or cobalt-chromium alloy tubes, another implantation process can be implemented, wherein: when graft fenestration at the fenestration area (121) is completed, the branch stent grafts are implanted in the branch arteries through a catheter, which can be followed by balloon expansion; balloon expansion can cause the temporary diversion channel to expand into a cylindrical shape, and its shape is permanently settled.

In this case, the bare stent (200) is not used, and only the stent graft (100) and the branch stent grafts are permanently implanted.

Example 7

Figure 9A:
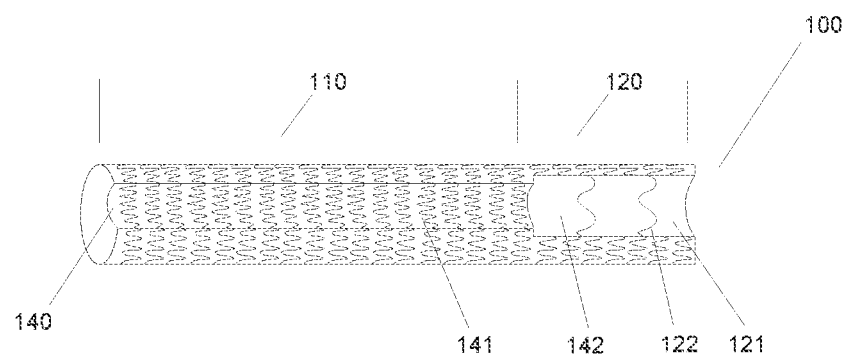
FIG. 9A shows a stent graft (100) with a temporary diversion channel, and its fenestration area with concave features is located at the end of the stent graft (100), that is, it only comprises a first stent graft section (110) and a second stent graft section (120) with a fenestration area; correspondingly, the temporary diversion channel (140) comprises a non-fenestration channel (141) and a fenestration area channel (142).
Figure 9B:
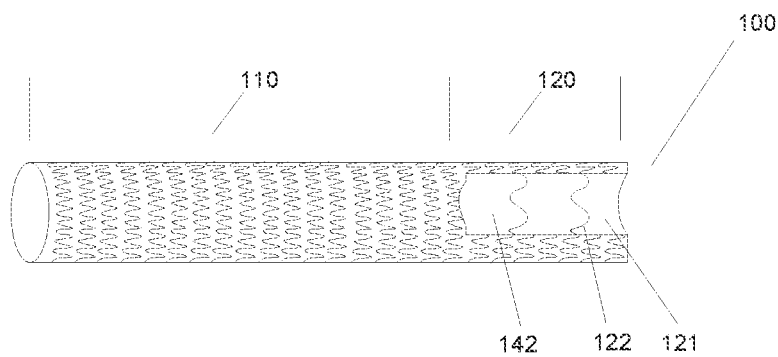
FIG. 9B shows that the temporary diversion channel (140) only comprises the fenestration area channel (142).
Figure 9C:
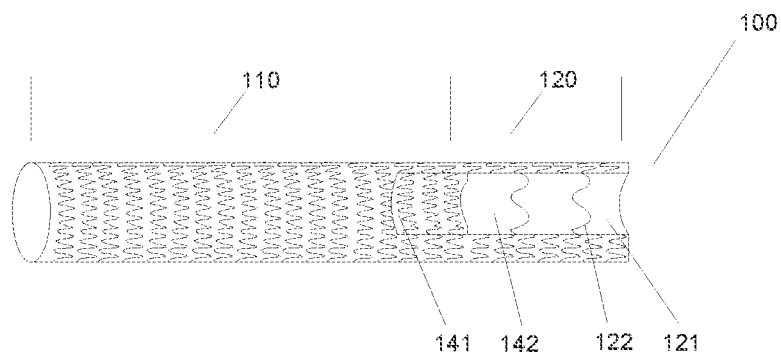
FIG. 9C shows that the temporary diversion channel (140) emerging from the fenestration area (121) and extends to but does not penetrate the first stent graft section (110).

As described above, for a stent graft (100) with a temporary diversion channel, its fenestration area with concave features can be located at the end of the stent, and can be applied in necessary treatment conditions, such as the treatment of descending aortic diseases affecting the left subclavian artery, or the treatment of abdominal aortic diseases affecting the renal artery, or other applicable conditions. As shown in FIG. 9A, the fenestration area (121) is located at the end of its stent graft (100), that is, it only comprises a first stent graft section (110) and a second stent graft section (110) with a fenestration area (120); correspondingly, the temporary diversion channel (140) comprises a non-fenestration channel (141) and a fenestration area channel (142). Alternatively, as shown in FIG. 9B, the temporary diversion channel (140) may only comprise a fenestration area channel (142). Or, starting from the fenestration area (121), it extends to the first stent graft section (110) but does not penetrate through, as shown in FIG. 9C.

Figure 10A:
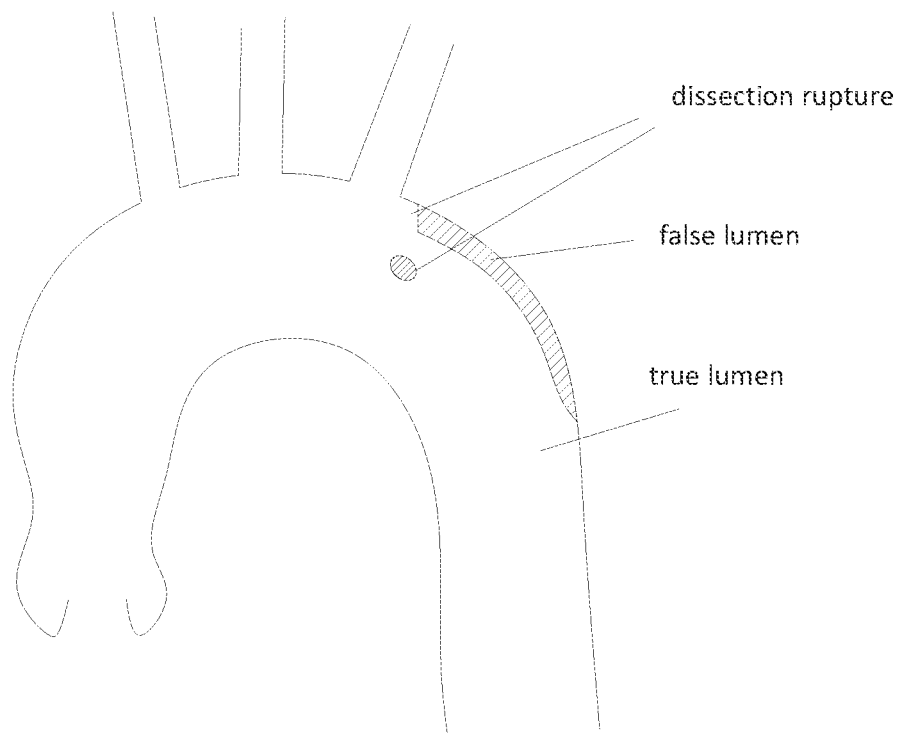
FIG. 10A shows the dissection of the descending aorta affecting the left subclavian artery.
Figure 10B:
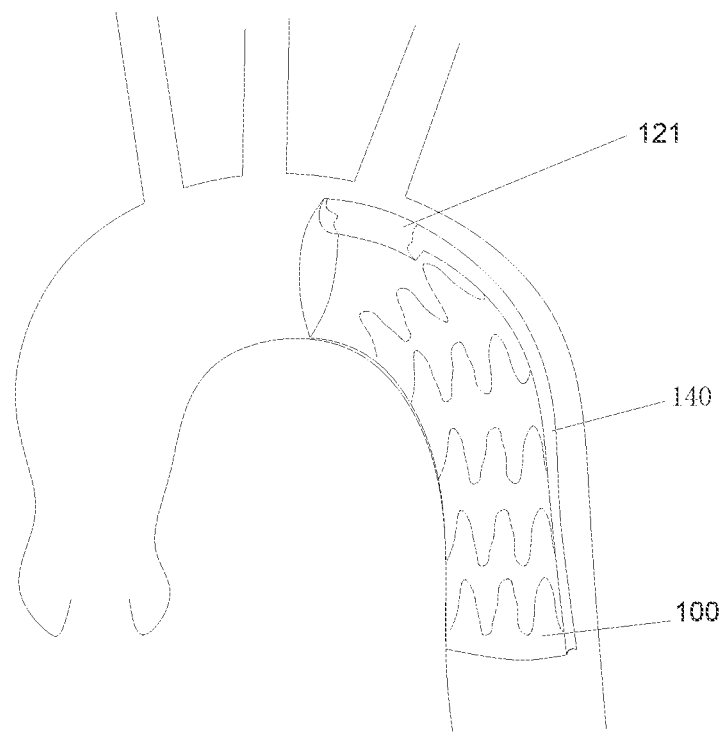
FIG. 10B shows a stent graft (100) with a temporary diversion channel, which is implanted via a transcatheter procedure. The dissection rupture is blocked by the stent graft, and the fenestration area with concave features is located at the end of the stent graft.

Taking a descending aortic dissection affecting the left subclavian artery as an example, the implantation process is as follows:

As shown in FIG. 10A, the dissection of the descending aorta affects the left subclavian artery;

As shown in FIG. 10B, the stent graft (100) with a temporary diversion channel is implanted via a transcatheter procedure. The dissection rupture is blocked by the stent graft, the fenestration area with concave features is located at the end of the stent graft, and the left subclavian artery can attain normal blood flow through the temporary diversion channel (140).

Figure 10C:
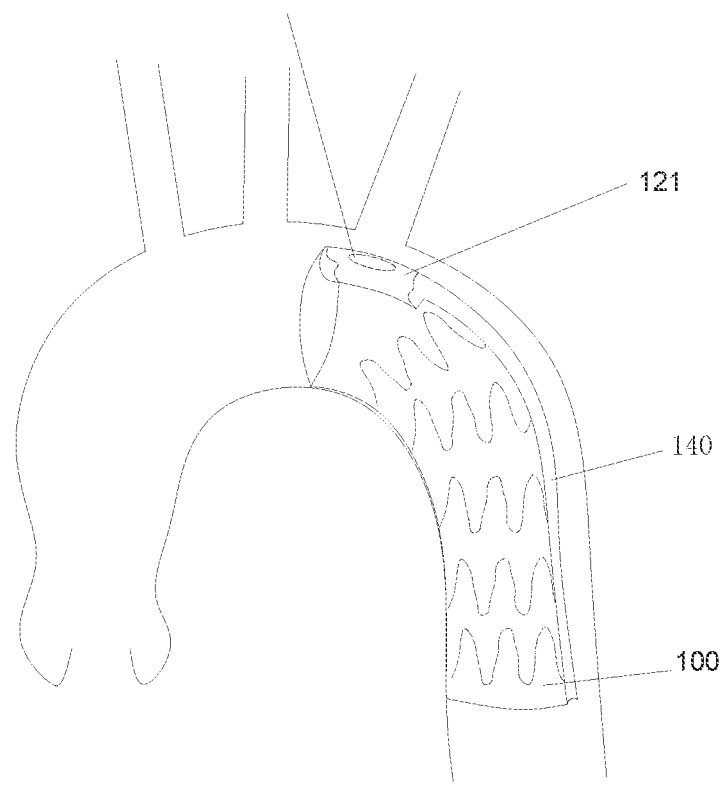
FIG. 10C shows that after the stent graft (100) is implanted, the fenestration area undergoes graft fenestration via the blood vessel path.
Figure 10D:
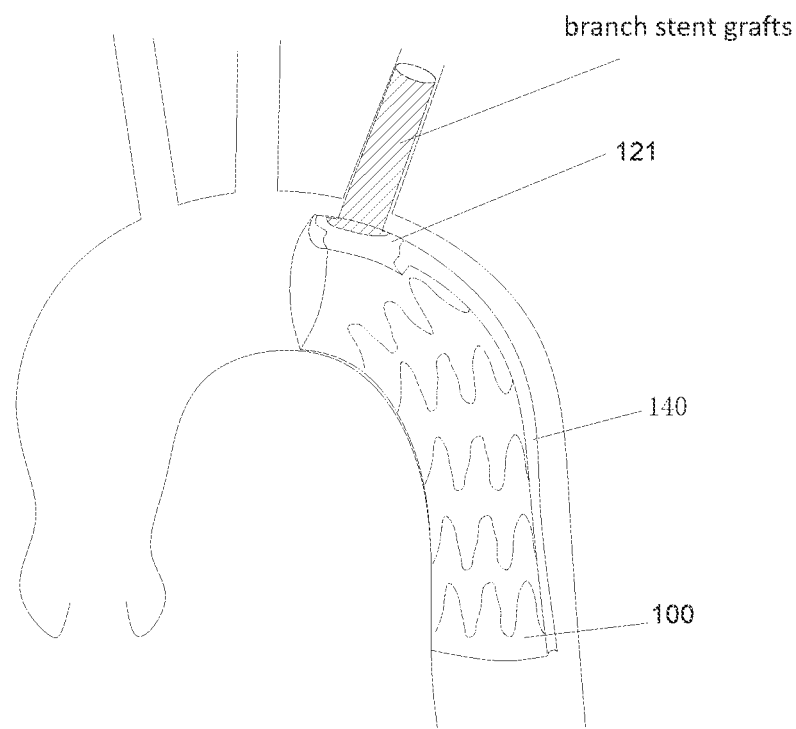
FIG. 10D shows that after the stent graft (100) is implanted and the fenestration area undergoes graft fenestration via the blood vessel path, a branch stent graft is further implanted into the left subclavian artery.

As shown in FIG. 10C, the fenestration area further undergoes graft fenestration via the blood vessel path, the fenestration area (121) of the stent graft (100) has no metal frame, or the concave frame is made of non-metallic materials, thereby avoiding any interference by the metal frame during the fenestration. Branch stent grafts (100) may be further implanted as shown in FIG. 10D. The fenestration area (121) of the stent graft (100) with no metal frame also ensures the smooth implantation and expansion of the branch stent graft.

Figure 10E:
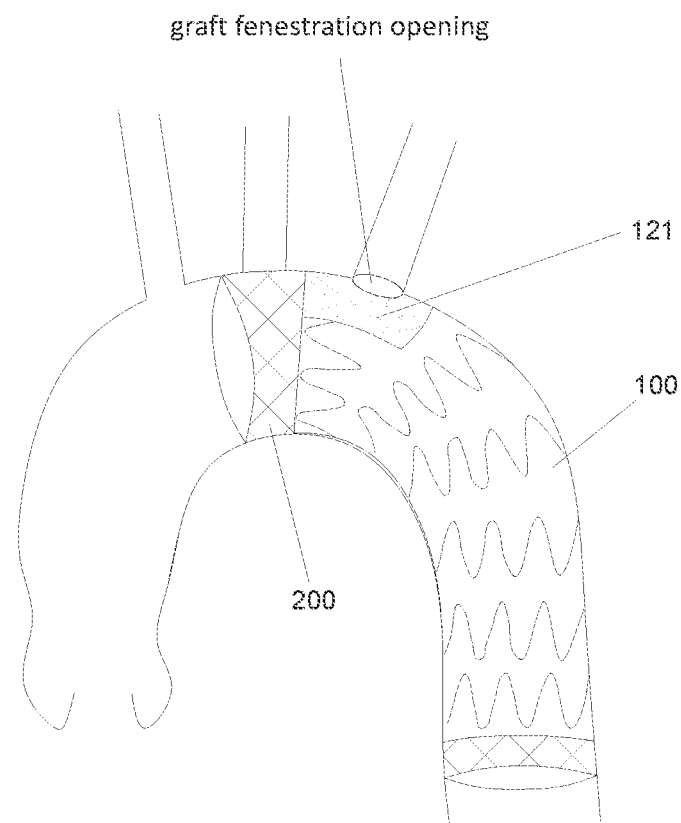
FIG. 10E shows a bare stent (200) being implanted via a transcatheter procedure, the temporary diversion channel (140) is expanded by the bare stent, and the graft is pushed against the blood vessel wall by the bare stent (200).
Figure 10F:
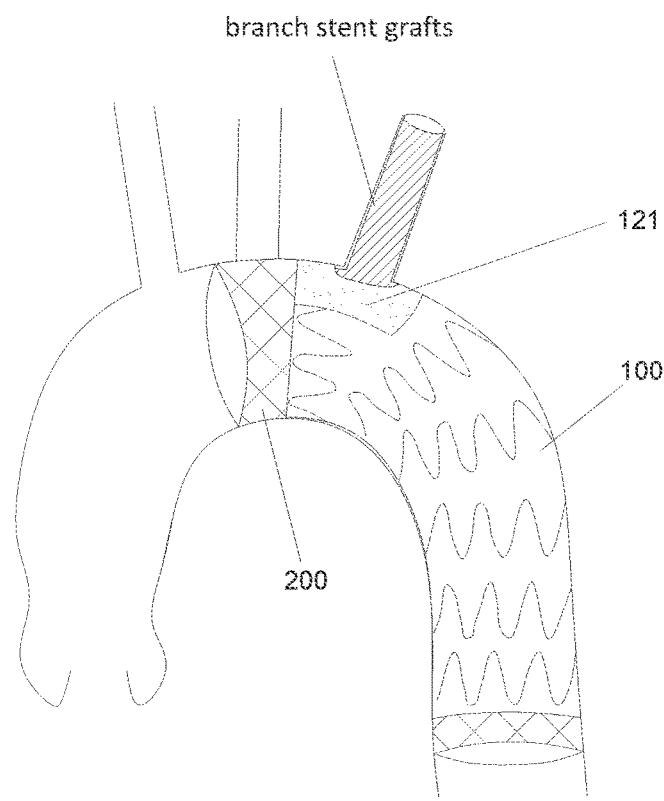
FIG. 10F shows the left subclavian artery with a branch stent graft implanted.

As shown in FIG. 10E, the bare stent (200) is implanted via a transcatheter procedure, the temporary diversion channel (140) is expanded by the bare stent, and the graft is pushed against the blood vessel wall by the bare stent (200). The situation of the branch stent graft being implanted in the left subclavian artery is as shown in FIG. 10F. The bare stent can be configured at the proximal end beyond the length of the stent graft, if necessary. Similarly, while the bare stent (200) expands the temporary diversion channel, the flared mouth at the proximal end of the branch stent graft is also pushed against the graft at the fenestration area to ensure that there is no endoleak.

Example 8

Figure 11A:
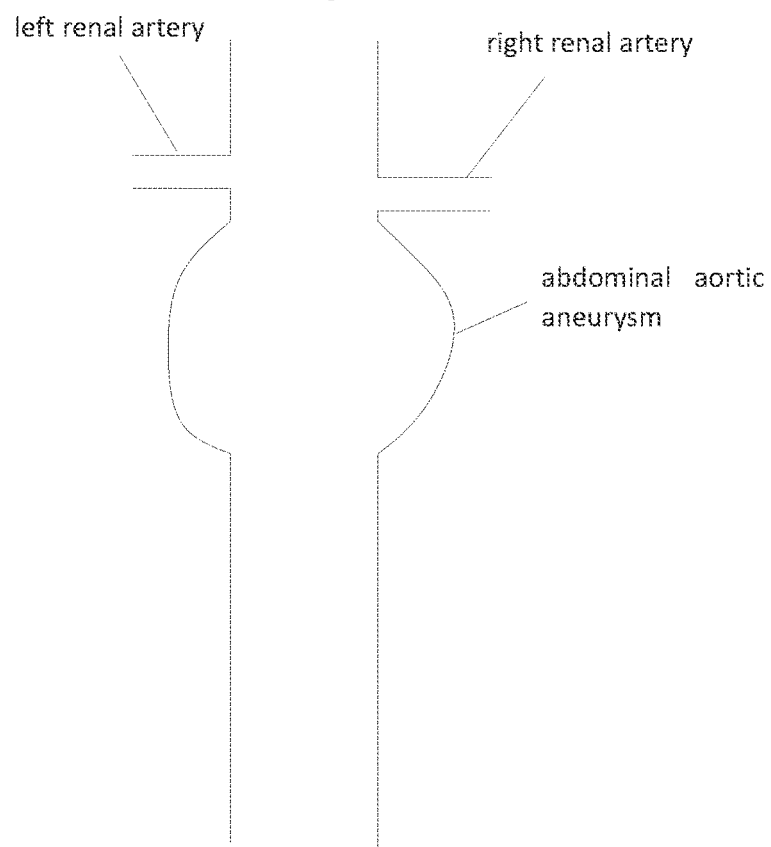
FIG. 11A shows that an abdominal aortic aneurysm being adjacent to the renal artery.
Figure 11B:
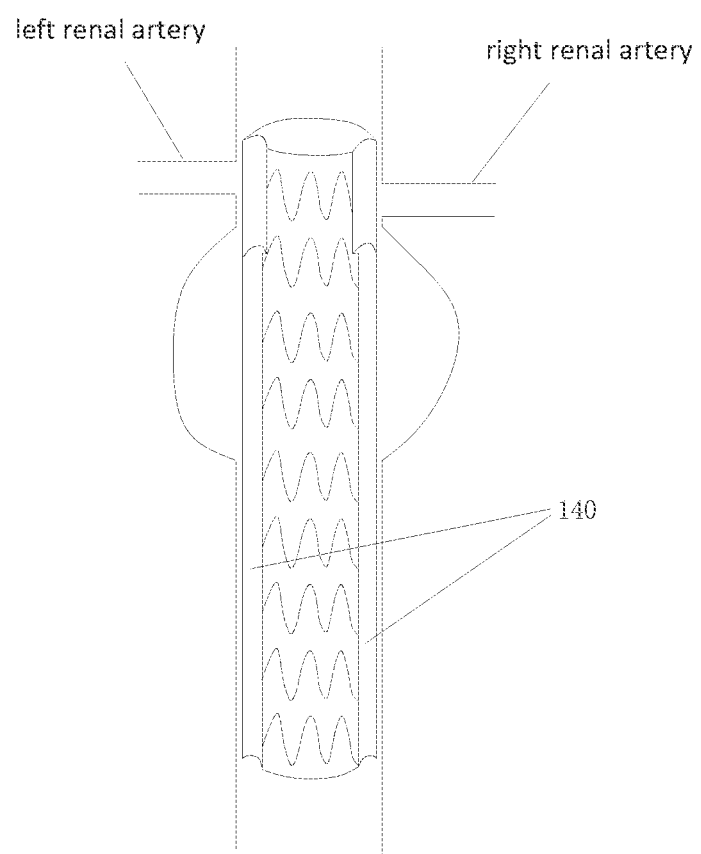
FIG. 11B shows a stent graft (100) with two temporary diversion channels being implanted via a transcatheter procedure.

Taking an abdominal aortic aneurysm affecting the renal artery as an example, the implantation process is as follows:

As shown in FIG. 11A, the abdominal aortic aneurysm is adjacent to the renal artery;

As shown in FIG. 11B, the stent graft (100) with two temporary diversion channels is implanted via a transcatheter procedure. The fenestration area with concave features is located at the end of the stent graft, and the left renal artery and right renal artery can obtain normal blood flow through the temporary diversion channel (140).

Figure 11C:
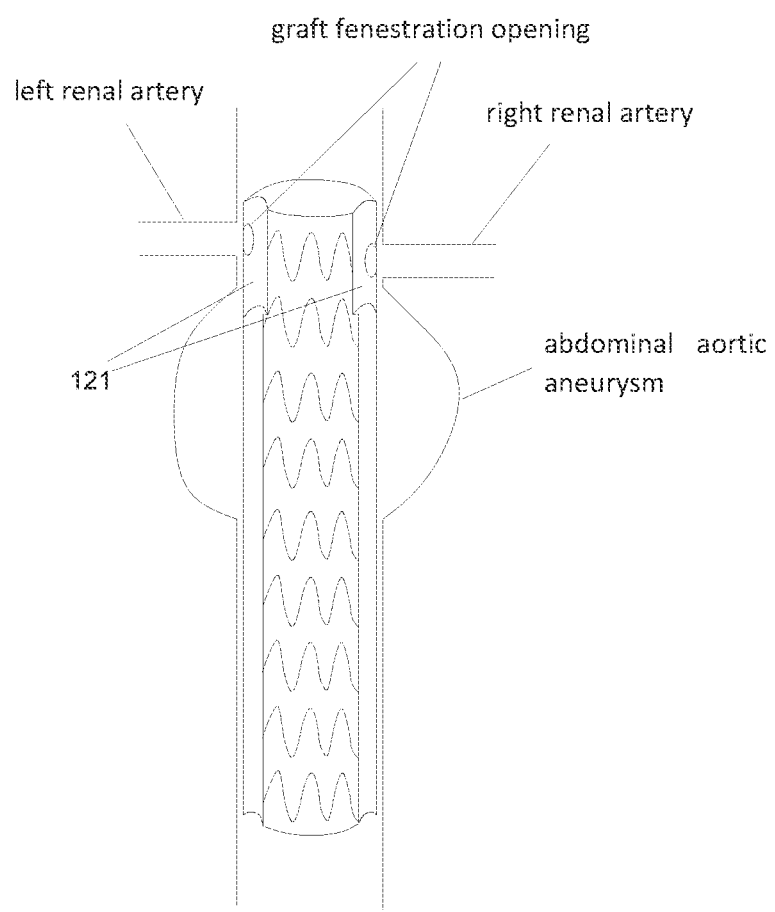
FIG. 11C shows that after the stent graft (100) is implanted, the fenestration area undergoes graft fenestration via the blood vessel path.
Figure 11D:
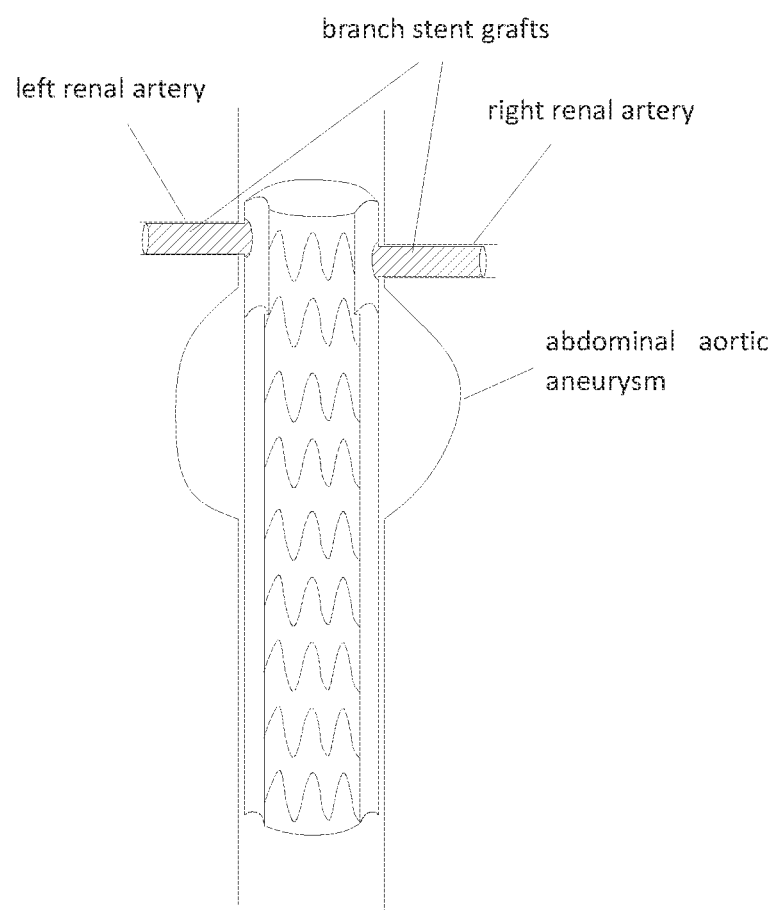
FIG. 11D shows that after the stent graft (100) has been implanted and the fenestration area underwent graft fenestration via the blood vessel path, branch stent grafts are further implanted into the left and right renal arteries.

As shown in FIG. 11C, the fenestration area further undergoes graft fenestration via the blood vessel path, the fenestration area (121) of the stent graft (100) has no metal frame, or the concave frame is made of non-metallic materials, thereby avoiding any interference by the metal frame during the fenestration. Branch stent grafts may be further implanted in the left renal artery and right renal artery as shown in FIG. 11D. The fenestration area (121) at the end of the stent graft (100) having no metal frame also ensures the smooth implantation and expansion of the branch stent graft.

Figure 11E:
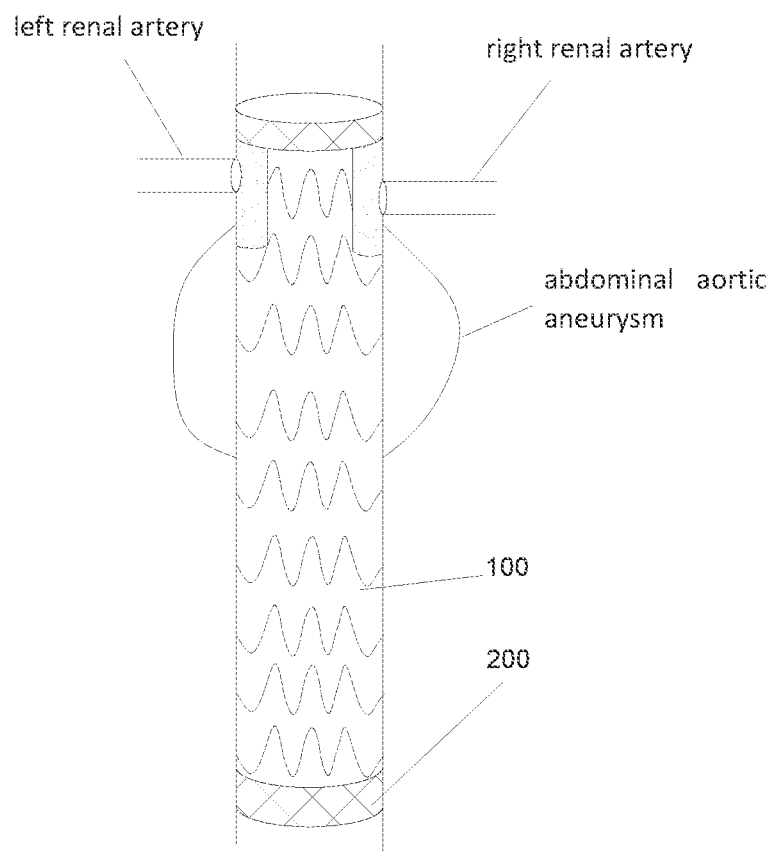
FIG. 11E shows the bare stent (200) being implanted via a transcatheter procedure, the temporary diversion channel (140) is expanded by the bare stent, and the graft is pushed against the blood vessel wall by the bare stent (200).
Figure 11F:
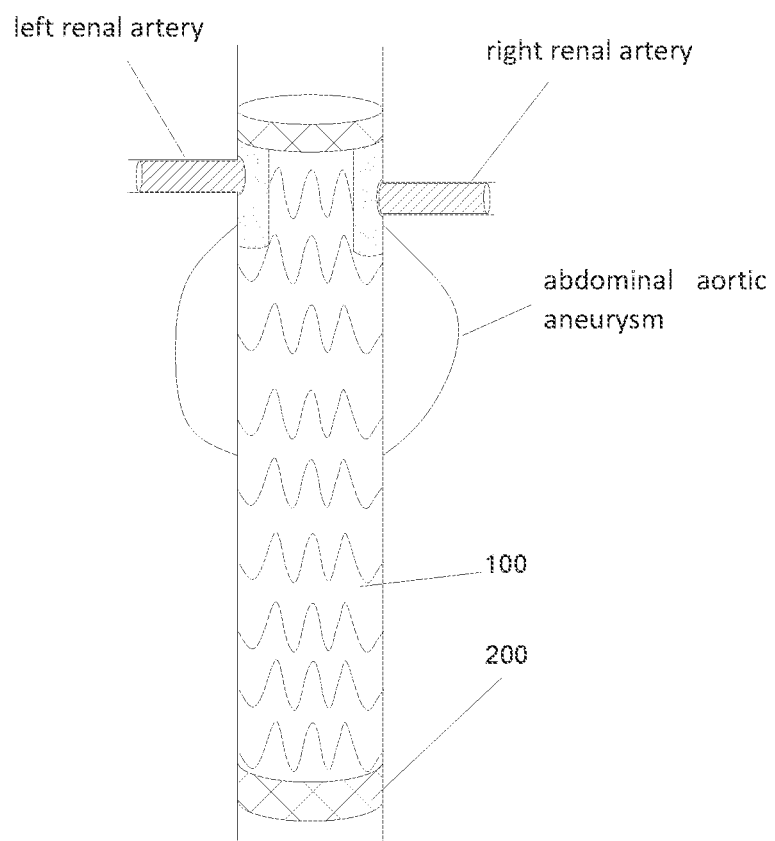
FIG. 11F shows the left and right renal arteries with branch stent grafts implanted.

As shown in FIG. 11E, the bare stent (200) is implanted via a transcatheter procedure, the temporary diversion channel (140) is expanded by the bare stent, and the graft is pushed against the blood vessel wall by the bare stent (200). The situation of the branch stent grafts being implanted in the left renal artery and right renal artery is as shown in FIG. 11F. Similarly, while the bare stent (200) expands the temporary diversion channel, the flared mouths at the proximal end of the branch stent grafts are also pushed tightly against the graft at the fenestration area to ensure that there is no endoleak.

The above implementation processes, which use the aortic arch as an example, will also be applicable to other positions of the aorta and to similar scenarios in the field of vascular applications; the above implementation processes which uses aortic dissection as an example, will also be applicable to aortic aneurysms and to similar scenarios in the field of vascular applications.

What is claimed is:

1. A stent graft, comprising a main body which comprises a frame and a graft, wherein:
    said main body comprises a fenestration area having only said graft; and
    said stent graft has a surface comprising at least one temporary diversion channel connected with said fenestration area; said stent graft comprises a control mechanism to control opening and closing of said at least one temporary diversion channel; said control mechanism is located in a part of said stent graft having at least one temporary diversion channel, the frame and the graft forming said at least one temporary diversion channel do not connect, at least one suture ring is provided on a same side and an opposite side of said at least one temporary diversion channel, and at least one control wire is provided for opening and closing said at least one temporary diversion channel of the graft.

2. The stent graft of claim 1, wherein said at least one temporary diversion channel is expandable to fix said stent graft into a circular cross-section.

3. The stent graft of claim 1, further comprising more than one fenestration areas, each fenestration area is separated by a concave skeletal structure.

4. The stent graft of claim 3, wherein said concave skeletal structure is connected or not connected to the frame of said main body.

5. The stent graft of claim 1, wherein said at least one temporary diversion channel comprise:
    a. a fenestration area channel (142); and
    b. a proximal channel (141) and/or a distal channel (143);
        wherein said fenestration area channel is wider than said proximal channel and/or said distal channel.

6. The stent graft of claim 1, wherein said fenestration area is located at an end of said main body and is concaved.

7. The stent graft of claim 1, wherein said main body comprises a first stent graft section, a second stent graft section, and a third stent graft section, said fenestration area is located in the second stent graft section.

8. The stent graft of claim 7, wherein said at least one temporary diversion channel is connected to the fenestration area of the second stent graft section via the first stent graft section or the third stent graft section.

9. The stent graft of claim 7, wherein said second stent graft section is more flexible than the first stent graft section or the third stent graft section.

10. The stent graft of claim 1, wherein said stent graft has a shape selected from the group consisting of a partially bulged outward shape, an inwardly concaved shape, a straight cylindrical shape, and a curved shape.

11. The stent graft of claim 1, wherein said at least one temporary diversion channels are distributed on the stent graft surface linearly along the stent graft length, or spiral-linearly along the stent graft surface.

12. The stent graft of claim 1, wherein said at least one temporary diversion channel is connected with at least one end of said stent graft.

13. A vascular reconstruction device, comprising:
    the stent graft of claim 1; and
    an expansion component to be placed in said stent graft for expansion, wherein said expansion component is to be expanded to larger than inner diameter of said stent graft.

14. The vascular reconstruction device of claim 13, wherein said expansion component is a bare stent.

15. The vascular reconstruction device of claim 14, wherein said bare stent comprises an area corresponding to said fenestration area, and said area comprises a sparse mesh.

16. The vascular reconstruction device of claim 13, wherein said expansion component is a balloon.

* * * * *